United States Patent
Bohrer et al.

(10) Patent No.: US 12,268,813 B2
(45) Date of Patent: Apr. 8, 2025

(54) BIOFILM REMOVAL DEVICE FOR ENDOTRACHEAL TUBES

(71) Applicants: Morgan Bohrer, Ridgefield, CT (US); Stephen Hahn, Johns Creek, GA (US); Michael L'Ecuyer, New Orleans, LA (US); Alexandra Verne, Northbrook, IL (US)

(72) Inventors: Morgan Bohrer, Ridgefield, CT (US); Stephen Hahn, Johns Creek, GA (US); Michael L'Ecuyer, New Orleans, LA (US); Alexandra Verne, Northbrook, IL (US)

(*) Notice: Subject to any disclaimer, the term of this patent is extended or adjusted under 35 U.S.C. 154(b) by 769 days.

(21) Appl. No.: 17/508,955

(22) Filed: Oct. 22, 2021

(65) Prior Publication Data

US 2022/0126043 A1    Apr. 28, 2022

Related U.S. Application Data

(60) Provisional application No. 63/104,521, filed on Oct. 23, 2020.

(51) Int. Cl.
*A61B 90/70* (2016.01)
*A61M 16/04* (2006.01)

(52) U.S. Cl.
CPC .... *A61M 16/0463* (2013.01); *A61M 16/0475* (2014.02); *A61B 90/70* (2016.02); *A61M 2205/02* (2013.01); *A61M 2209/10* (2013.01)

(58) Field of Classification Search
CPC .......... A61M 16/0463; A61M 16/0475; A61M 2205/02; A61M 2209/10; A61M 1/83;
(Continued)

(56) References Cited

U.S. PATENT DOCUMENTS

| | | | | |
|---|---|---|---|---|
| 4,696,296 A | * | 9/1987 | Palmer | A61M 16/0463 251/95 |
| 5,709,691 A | * | 1/1998 | Morejon | A61M 1/83 128/207.14 |

(Continued)

*Primary Examiner* — Timothy A Stanis
*Assistant Examiner* — Kira B Daher
(74) *Attorney, Agent, or Firm* — David M. Stein

(57) ABSTRACT

A device for biofilm removal from an endotracheal tube is disclosed. Such a device may include a hollow catheter having a tip, wherein said device is inserted down an endotracheal tube of an orally intubated patient. Said tip may include a cylindrical central portion and a fin configured to dislodge biofilm from the inner lumen of the endotracheal tube as the device is rotated, either manually or mechanically, inside the endotracheal tube. The fin may be configured as a helix and positioned to spiral around said cylindrical central portion of the tip thereby forming a channel, defined by the pitch of said helix, about the circumference of the cylindrical central portion. Biofilm dislodged from the inner surface of the endotracheal tube by the rotational motion of the fin may be retained within the channel until the tip is removed from the endotracheal tube. The device may further comprise a motor for mechanically rotating the catheter and tip. Finally, the device may be configured to interface with a mechanical ventilator such that airflow to an intubated patient is not impeded while said device is used to remove biofilm from the inner surface of the patient's endotracheal tube.

8 Claims, 8 Drawing Sheets

(58) Field of Classification Search
CPC .... A61M 1/74–743; A61M 2025/0019; A61B 2090/701; A61B 90/70; A61B 1/00073
USPC ........................................................ 606/106
See application file for complete search history.

(56) References Cited

U.S. PATENT DOCUMENTS

| | | | | |
|---|---|---|---|---|
| 6,699,331 | B1* | 3/2004 | Kritzler | A61B 1/122 134/8 |
| 7,503,328 | B2* | 3/2009 | Kolobow | A61M 16/0463 128/207.14 |
| 2005/0172971 | A1* | 8/2005 | Kolobow | A61M 16/0463 128/207.14 |
| 2010/0217296 | A1* | 8/2010 | Morriss | A61M 1/84 606/162 |
| 2011/0023888 | A1* | 2/2011 | Vazales | A61B 1/00142 128/207.14 |
| 2011/0197894 | A1* | 8/2011 | Morejon | A61M 16/0463 128/207.14 |
| 2014/0090642 | A1* | 4/2014 | Bagwell | A61M 16/04 128/202.13 |
| 2014/0102445 | A1* | 4/2014 | Clement | A61M 1/77 128/202.13 |
| 2016/0135661 | A1* | 5/2016 | Ailinger | G02B 23/2476 600/114 |
| 2018/0311709 | A1* | 11/2018 | Rowe | A61B 90/70 |
| 2018/0326169 | A1* | 11/2018 | Rosengart | A46B 13/00 |

\* cited by examiner

BIOFILM REMOVAL DEVICE FOR ENDOTRACHEAL TUBES

CROSS-REFERENCES TO RELATED INVENTIONS

This Application claims the benefit of prior-filed provisional application 63/104,521, Confirmation Number 5400, entitled, "Biofilm Removal Device for Endotracheal Tubes," filed on Oct. 23, 2020.

FIELD OF THE INVENTION

The present invention is generally related to medical devices, and, more particularly, to a device for removing biofilm from the interior surface of an endotracheal tube without removing said tube from the trachea of an orally intubated patient.

STATEMENTS AS TO THE RIGHTS TO INVENTIONS MADE UNDER FEDERALLY SPONSORED RESEARCH OR DEVELOPMENT

Not applicable.

REFERENCE TO A "SEQUENCE LISTING," A TABLE, OR A COMPUTER PROGRAM LISTING APPENDIX SUBMITTED ON A COMPACT DISK

Not applicable.

BACKGROUND OF THE INVENTION

When a patient is unable to protect their airway or breathe on their own, they are typically orally intubated and placed on a ventilator. If the endotracheal tube (ETT) is left in for more than two days, biofilm may build up on the inner lumen of the tube, restricting air flow and leading to potentially serious complications. This biofilm buildup directly leads to 80% of antibiotic resistant infections, the most common being ventilator associated pneumonia (VAP)—a lung infection that may develop 48 hours or longer after the start of mechanical ventilation. This form of pneumonia occurs in 12-25% of all intubated patients, and is fatal in 24-71% of those cases. Biofilm buildup also increases airflow resistance by decreasing the diameter of the ETT, resulting in more difficult spontaneous breathing tests for the patients. Currently, the most prevalent solution to an unacceptable amount of inner lumen biofilm build-up is to perform a tracheotomy on the patient.

Tracheotomies are more invasive, result in a scar, and have the potential for long term airway injuries to the patients. Taken alone, the tracheotomy procedure carries certain risks, including bleeding and infection at the incision site, esophageal damage, and pneumothorax. But the 2019 novel coronavirus outbreak presents even greater challenges. Due to the highly infectious nature of coronavirus disease 2019 (COVID-19), many healthcare providers are electing to delay tracheotomies for as long as possible to limit patients' potential exposure to the coronavirus. Typically, tracheotomies are commonly performed within 10 to 15 days of a patient being intubated. But since the advent of the COVID-19 pandemic, doctors have delayed tracheotomies by an additional 7 to 10 days. These delays increase those patients' risk of developing VAP due to biofilm build-up in the ETTs.

Biofilm build-up can also unnecessarily prolong the amount of time a patient remains on a ventilator. Medical professionals may determine a patient's readiness to breath independently (i.e. without ventilator assistance) through spontaneous breathing trials (SBTs). SBTs are conducted by turning off the ventilator and measuring the patient's breath depth. But the longer a patient is intubated, the more difficult it becomes for the patient to pass an SBT, because the inner diameter of the endotracheal tube decreases as biofilm accumulates on the inner lumen. The smaller diameter is more difficult for the patient to breathe through, as the decrease in inner diameter results in an increase in the air resistance through the ETT. The patient may thus fail the SBT, leading to increased time on the ventilator.

If the biofilm were removed from ETTs, the risk of VAP would be greatly decreased, there would be less need for health care providers to perform tracheotomies, and intubated patients would be more likely to pass SBTs sooner. It is therefore an object of this invention to provide a device for removing biofilm from the inner lumen of endotracheal tubes while said tube is still in place in an intubated patient.

One current method for removing biofilm within an ETT is through the use of a closed-loop suction catheter. However, studies to determine the effectiveness of suctioning with respect to decreasing the risk of VAP have been inconclusive. Moreover, in order to use the suction catheter, a health care provider must remove the patient from the ventilator for 15 sections. Many patients have described such suction cleaning as a feeling of suffocation. Accordingly, while the suction catheter can help increase the inner diameter of the ETT in advance of an SBT by removing loose biofilm, the procedure does not significantly reduce the risk of VAP, since it cannot remove biofilm adhered to the walls of the ETT. Moreover, the suction procedure results in patient distress as it is being performed.

Currently available devices for removing biofilm from ETTs may feature a balloon that is expanded radially once the device is inserted into the ETT (See, e.g., US 2011/0186052 A1, U.S. Pat. Nos. 7,051,737 B2, 6,494,208 B1, and 8,468,637 B2). After the balloon expands, such devices are lifted out of the ETT, scraping mucus and bacteria off the sides. However, such devices are configured only to remove loose debris from the interior lumen of ETT tubes. It is therefore a further object of the present invention to provide a device capable of dislodging and removing biofilm that has become adhered to the inner lumen of ETT tubes such that the device is configured to present a consistent shearing of biofilms as it traverses the ETT.

SUMMARY OF THE INVENTION

According to an exemplary embodiment of the present invention, a device for biofilm removal from endotracheal tubes may include a catheter having a firm tip, wherein said device is inserted down an endotracheal tube of an orally intubated patient, wherein said endotracheal tube is connected to a ventilator. Said tip may further comprise a cylindrical central portion and one or more fins configured to dislodge debris, such as biofilm, from the inner lumen of the endotracheal tube as the device is rotated, either manually or mechanically, inside the endotracheal tube. Each of the one or more fins may be configured as a helix and positioned to spiral around said cylindrical central portion of the tip thereby forming one or more channels, defined by the pitch of said helix, about the circumference of the cylindrical central portion. The tip may further include a hollow canal through the central portion configured to allow airflow to pass to the patient from the ventilator during the cleaning process. The device may further comprise a motor for mechanically rotating the catheter and tip. The tip may be further configured such that biofilm dislodged from the inner surface of the endotracheal tube is retained in the one or more channels defined by the pitch of the one or more helical fins until the tip is removed from the tube, or the device may include a vacuum device positioned to remove dislodged biofilm from the spaces between the one or more fins while the tip is still within the endotracheal tube. The tip may be further configured to apply sufficient force to the inner lumen of the endotracheal tube to remove biofilm therefrom while simultaneously causing no damage to the endotracheal tube.

DETAILED DESCRIPTION

A device for removing biofilm may be configured to clean the inner lumen of an endotracheal tube of an orally intubated patient without damaging the tube and without the need for extubating the patient. Accordingly, an exemplary embodiment of the present invention may include a hollow catheter having a tip at the distal end, wherein said device is configured to be inserted, tip-first, down an endotracheal tube of an orally intubated patient. Said tip may further comprise a cylindrical central portion and one or more fins configured to extract debris from the inner lumen of the endotracheal tube as the device is rotated, either manually or mechanically, inside the endotracheal tube. Each of the one or more fins may be configured as a helix positioned to spiral around said cylindrical central portion of the tip, thereby forming one or more channels, defined by the pitch of said helix, about the circumference of the cylindrical central portion. Thus, the device may be configured and positioned such that the fins shear or scrape biofilm off of the inner lumen of an endotracheal tube as the device is rotated. The device may be further configured such that biofilm removed from the inner lumen of the endotracheal remains in the channels defined by the pitch of the helical fin or fins until the device is extracted from the tube. Other embodiments of the present invention may further comprise a vacuum device positioned to apply a suction force such that biofilm is removed from the channels of the tip prior to the device being extracted from the tube. The tip may further include a hollow canal through the cylindrical central portion configured to align with the hollow portion of the catheter to allow for the passage of air, thereby allowing the endotracheal tube to be connected to a ventilator during the cleaning process without impeding the patient's airflow. The device may further comprise a housing attached to the proximal end of the hollow catheter and configured interface with a ventilator such that airflow to and from the intubated patient is not interrupted during the use of the device. The device may further comprise a motor attached to said housing configured to mechanically rotate the catheter and tip. Moreover, the material and/or geometry of the tip may be further configured to apply sufficient force to the inner lumen of the endotracheal tube to remove biofilm therefrom while simultaneously causing no damage to the endotracheal tube.

Figure 1:
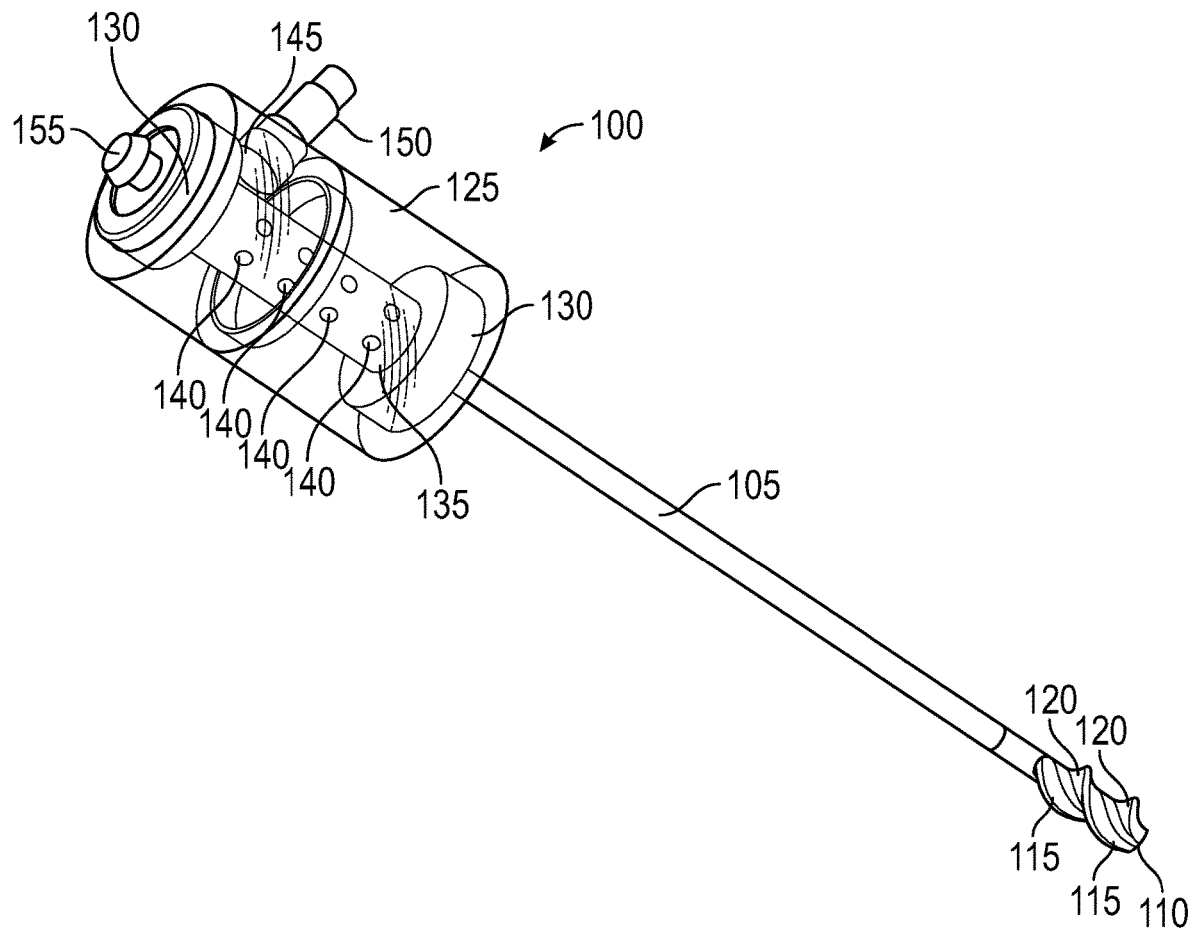
FIG. 1 is a front perspective view of a device for removing biofilm from an endotracheal tube, accordingly to an exemplary embodiment of the present invention.

FIG. 1 is a front perspective view of a device 100 for removing biofilm from an endotracheal tube, accordingly to an exemplary embodiment of the present invention. Device 100 may include hollow catheter 105 and tip 110 attached to the distal end of catheter 105. Tip 110 may comprise a hollow cylindrical central portion and a fin 115 and configured such that fin 115 wraps around said hollow cylindrical portion in the shape of a helix having a pitch such that fin 115 defines a channel 120 adjacent to the cylindrical central portion between the pitch of fin 115. Tip 110 may further comprise a hollow longitudinal channel through the cylindrical central portion that, when attached to catheter 105, aligns with the hollow center of catheter 105 to allow the passage of air through catheter 105 and tip 110. Thus, device 100 may be configured such that the longitudinal axis of catheter 105 and tip 110 are aligned.

Device 100 may be further configured such that the combination of catheter 105 and tip 110 are configured to rotate about their respective longitudinal axes such that fin 115 has a rotational motion. Thus, when the combination of catheter 105 and tip 110 are inserted into an endotracheal tube having an accumulation of biofilm along its inner lumen, device 100 is thus configured such that fin 115 contacts the inner lumen of the endotracheal tube such that the rotational motion of fin 115 dislodges said biofilm from the inner lumen of the endotracheal tube as tip 110 traverses the interior of said endotracheal tube. Device 100 may be further configured such that said dislodged biofilm is retained within channel 120 until catheter 105 and tip 110 are removed from said endotracheal tube.

According to some embodiments of the present invention, device 100 may further comprise housing 125, which may include bearing and seal combinations 130 and shaft 135. Shaft 135 may connect to the proximal end of hollow catheter 105 and be configured to rotate the combination of catheter 105 and tip 110 about their respective longitudinal axes such that fin 115 has a rotational motion. Shaft 135 may further comprise a hollow longitudinal channel having a longitudinal axis and a plurality of holes 140. Thus, shaft 135 may be configured such that its hollow longitudinal channel aligns with the hollow center of catheter 105 to allow the passage of air and other gases to and from catheter 105. Said plurality of holes 140 may be configured to allow the passage of said air and other gases to pass to/from the hollow longitudinal channel of shaft 135 to/from the interior of housing 125. In certain embodiments, bearing and seal combinations 130 allow shaft 135 and catheter 105 to pass through the surface of housing 125 while keeping the interior environment of housing 125 sealed off from the environment outside of device 100.

In some embodiments of the present invention, housing 125 may further comprise opening 145 and motor 155. Opening 145 may be configured to receive ventilator hose 150. Thus, device 100 may be configured to allow the passage of air and other gases to and from a ventilator through device 100 as device 100 is used to clean the inner lumen of an endotracheal tube of an intubated patient. Specifically, while device 100 is inserted into an endotracheal tube of an intubated patient, air and other gases, such as oxygen, may be delivered to said endotracheal tube from said ventilator through hose 150. Said air and other gasses may then travel through plurality of holes 140 into the hollow longitudinal channel of shaft 135, into hollow catheter 105, and then into said endotracheal tube through tip 110. Other gases, such as carbon dioxide, may travel back to said ventilator via the reverse of the aforementioned path, i.e., through tip 110 into hollow catheter 105, into shaft 135, through holes 140 into the interior of housing 125, then back to the ventilator through opening 145 and hose 150.

Device 100 may be further configured such that when the combination of catheter 105 and tip 110 are inserted into an endotracheal tube, housing 125 remains outside of said endotracheal tube. In certain embodiments, a portion of shaft 135 may be configured to protrude from housing 125 through bearing and seal combination 130 positioned at the proximal end of housing 125. Accordingly, in said embodiments, shaft 135—and thus hollow catheter 105 and tip 110—may be rotated by the application of a torque to said portion of shaft 135 protruding from the proximal end of housing 125. Such torque may be accomplished manually or through the use of motor 155.

Figure 2C:
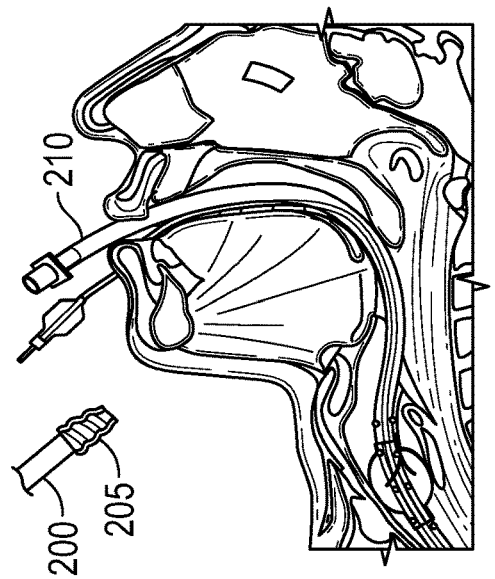
FIGS. 2a-2c are side views of a device for removing biofilm from an endotracheal tube being used to remove biofilm from the inner lumen of the endotracheal tube of an orally intubated patient, according to an exemplary embodiment of the present invention.
Figure 2B:
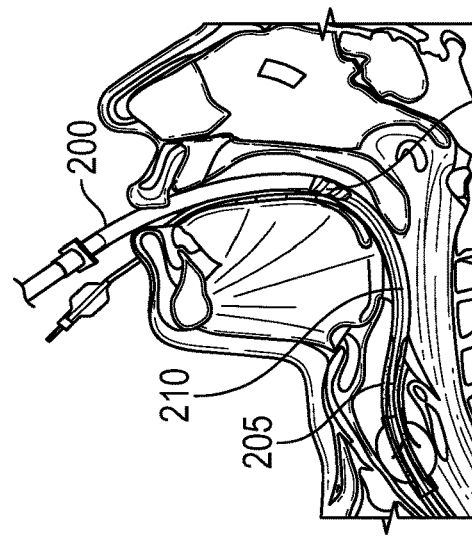
Figure 2A:
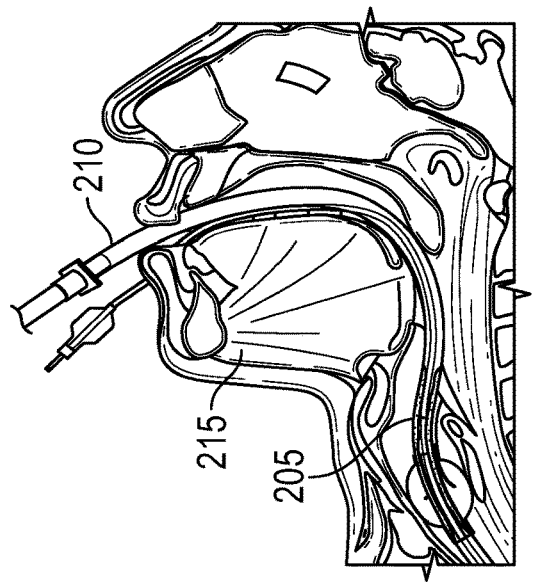

FIGS. 2a-2c are side views of a device for removing biofilm from an endotracheal tube being used to remove biofilm from the inner lumen of the endotracheal tube of an orally intubated patient, according to an exemplary embodiment of the present invention. In FIG. 2a, biofilm 205 has built up inside the inner lumen of endotracheal tube 210 in intubated patient 215, thereby restricting patient 215's airflow and increasing patient 215's risk of various infections, and lessening patient 215's likelihood of passing a spontaneous breathing trial. FIG. 2b illustrates device 200 having a tip 220, according to an exemplary embodiment of the present invention, being inserted into endotracheal tube 210 towards biofilm 205. Device 200 may be rotated, either manually or mechanically, as it traverses endotracheal tube 210 such that one or more fins positioned on tip 220 contact the inner lumen of endotracheal tube 210 and shear or otherwise dislodge biofilm 205 from the inner lumen of endotracheal tube 210. The one or more fins positioned on tip 220 may by further configured such that biofilm removed from the inner lumen of endotracheal tube 210 remains in channels between the one or more fins about tip 220 until device 200 is extracted from endotracheal tube 220, as illustrated in FIG. 2c, thereby removing biofilm 205 from endotracheal tube 210.

Figure 3:
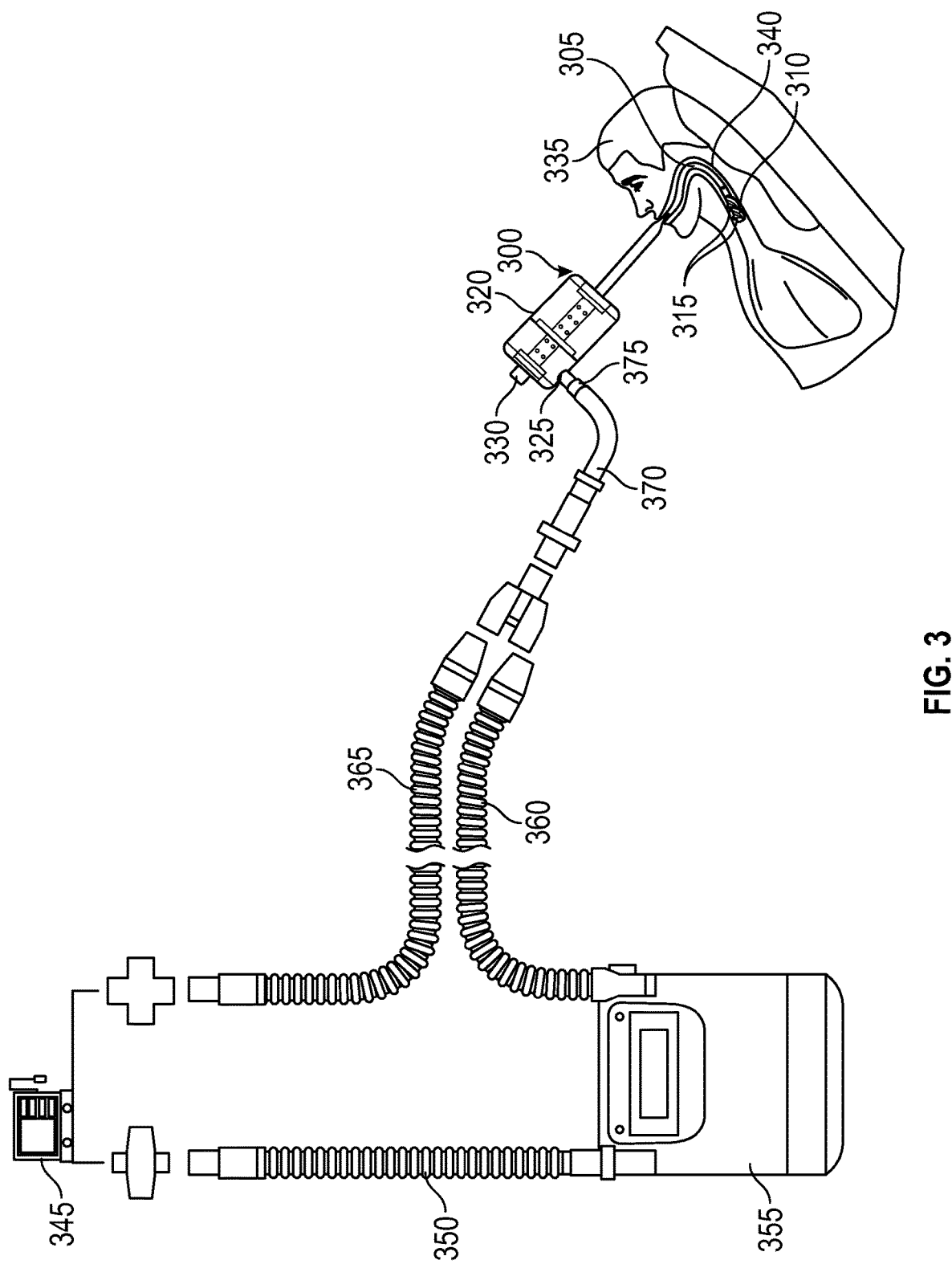
FIG. 3 is a side view of a device for removing biofilm from an endotracheal tube interfacing with a ventilator such that airflow to an intubated patient is not interrupted during use of said device, according to an exemplary embodiment of the present invention.

FIG. 3 is a side view of a device 300 for removing biofilm from an endotracheal tube 350 (positioned to) interface with ventilator 345 such that airflow provided by ventilator 345 to intubated patient 335 is not interrupted during use of device 300, according to an exemplary embodiment of the present invention. Device 300 may comprise hollow catheter 305, tip 310, fin 315 positioned around the circumference of tip 310 in the shape of a helix, and housing 320. In some embodiments, housing 320 may further comprise opening 325 and motor 330 configured to rotate the combination of catheter 305 and tip 310. In certain embodiments of the present invention wherein patient 335 is intubated with endotracheal tube 340 and mechanically ventilated via ventilator 345, ventilator 345 may be configured to deliver breathable air to humidifier 355 via delivery tube 350. Humidifier 355 may be configured to add moisture to said breathable air and/or to regulate the temperature of said breathable air before delivery to patient 335 via delivery hose 360. Used air hose 365 may be configured to return expired air, such as carbon dioxide, from patient 335 to ventilator 345. According to an exemplary embodiment of the present invention, device 300 may be configured such that airflow from ventilator 345 to patient 335 is not interrupted when device 300 is used to clean or remove biofilm from the inner lumen of endotracheal tube 340. Accordingly, certain embodiments of device 300 are configured such that breathable air and other such gases may pass through tip 310, hollow catheter 305, and opening 325 such that mechanical ventilation from ventilator 345 to patient 335 is not interrupted while catheter 305 and tip 310 are inserted into endotracheal tube 340 for the removal of biofilm therefrom. Thus, in certain embodiments of the present invention, opening 325 is configured to interface with hose 370 at connection 375 such that mechanical ventilation to patient 335 may continue while device 300 is used to clean biofilm from the inner surface of endotracheal tube 340.

FIGS. 4a-4d are front views of various iterations of tips 400, 405, and 410 for a device for removing biofilm from an endotracheal tube, according to exemplary embodiments of the present invention. Each iteration of tips 400, 405, and 410 have a cylindrical central portion 415 having a hollow longitudinal channel, and at least one fin. While the geometry of said fin may be any shape configured to dislodge biofilm from the interior of an endotracheal tube as tip 400, 405, or 410 is rotated therein, experimentation performed by the inventors listed herein yielded two shapes suitable for the removal of biofilm from endotracheal tubes. The first shape, illustrated in FIGS. 4a and 4b as fins 420 and 430, is an approximate trapezoidal prism positioned about cylindrical central portion 415 as a helix having a pitch. Thus, the two-dimensional profile of fins 420 and 430 may be approximately the shape of an isosceles trapezoid having a larger base, a smaller base, and two sides, wherein the larger base connects to the surface of cylindrical central portion 415. The opposition end of the profile of fins 420 and 430, i.e., the smaller base of said trapezoid, which is configured to make contact with the inner lumen of an endotracheal tube and to dislodge biofilm therefrom, may be configured as a rounded tip, rather than having the sharp edges of a true trapezoid, to avoid damage to said endotracheal tube as the device rotates therein. The second shape, illustrated in FIGS. 4c and 4d as fins 425 and 435, is an approximate triangular prism positioned about cylindrical central portion 415 as a helix having a pitch. Thus, the two-dimensional profile of fins 425 and 435 may be approximately the shape of a right triangle having a base and a height, wherein the base connects to the surface of cylindrical central portion 415. The opposite end of the profile of fins 425 and 435, which is configured to make contact with the inner lumen of an endotracheal tube and to dislodge biofilm therefrom, may be configured as a rounded tip, rather than the sharp edge of a true triangle, to avoid damage to said endotracheal tube as the device rotates therein.

Figure 4B:
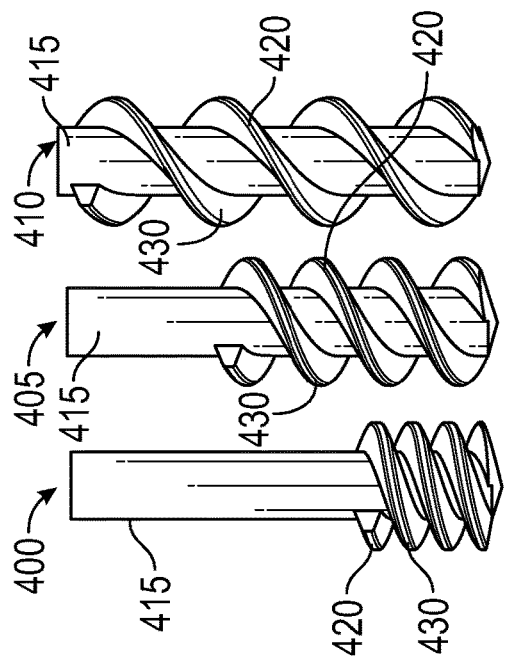
FIGS. 4a-4d are front views of tips for a device for removing biofilm from an endotracheal tube, according to exemplary embodiments of the present invention.
Figure 4D:
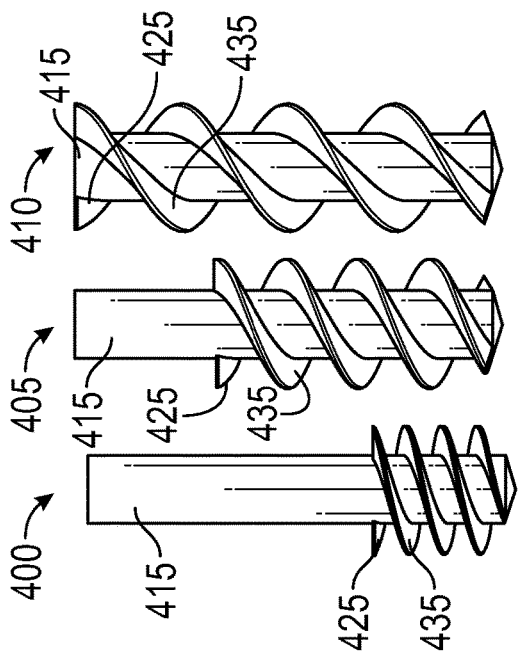
Figure 4A:
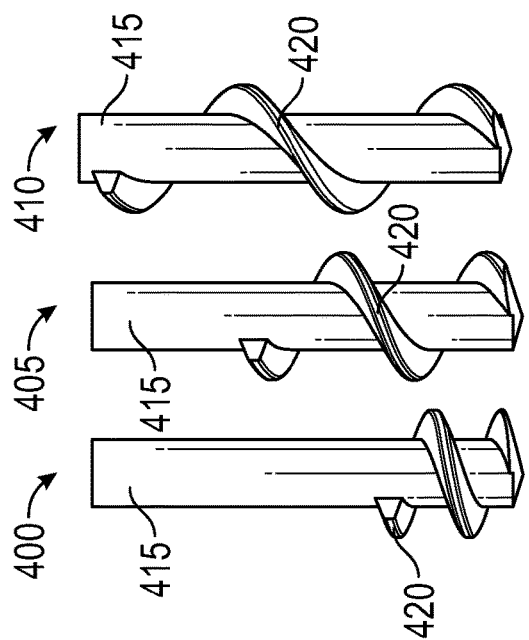

According to exemplary embodiments of the present invention, tips 400, 405, and 410 may comprise cylindrical central portion 415 and fin 420. While the pitch of fin 420 may be any dimension configured to accomplish the removal of biofilm from the inner lumen of an endotracheal tube as tip 400, 405, or 410 is rotated therein, FIG. 4a illustrates tip 400 wherein the pitch of fin 420 is 5 mm, tip 405 wherein the pitch of fin 420 is 10 mm, and tip 415 wherein the pitch of fin 420 is 15 mm. In other embodiments, tips 400, 405, and 410 may have two fins 420 and 430 positioned about cylindrical central portion 415 as helixes having a pitch. While the pitch of fins 420 and 430 may be any dimension configured to accomplish the removal of biofilm from the inner lumen of an endotracheal tube as tip 400, 405, or 410 is rotated therein, FIG. 4b illustrates tip 400 wherein the pitch of fins 420 and 430 is 5 mm, tip 405 wherein the pitch of fins 420 and 430 is 10 mm, and tip 415 wherein the pitch of fins 420 and 430 is 15 mm.

Figure 4C:
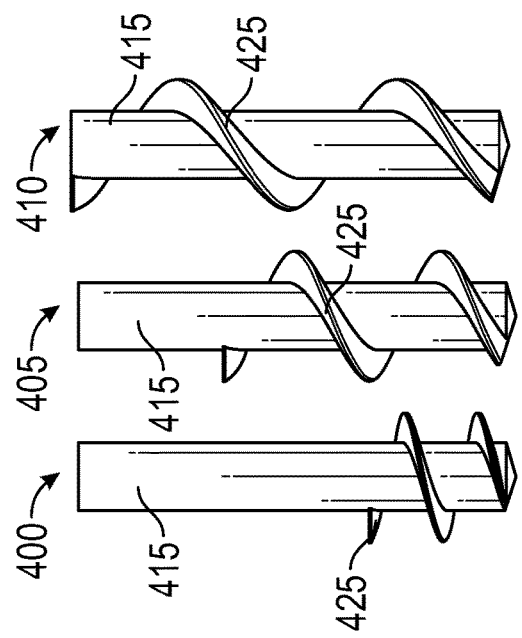

According to exemplary embodiments of the present invention, tips 400, 405, and 410 may comprise cylindrical central portion 415 and fin 425. While the pitch of fin 425 may be any dimension configured to accomplish the removal of biofilm from the inner lumen of an endotracheal tube as tip 400, 405, or 410 is rotated therein, FIG. 4c illustrates tip 400 wherein the pitch of fin 425 is 5 mm, tip 405 wherein the pitch of fin 425 is 10 mm, and tip 415 wherein the pitch of fin 425 is 15 mm. In other embodiments, tips 400, 405, and 410 may have two fins 425 and 435 positioned about cylindrical central portion 415 as helixes having a pitch. While the pitch of fins 425 and 435 may be any dimension configured to accomplish the removal of biofilm from the inner lumen of an endotracheal tube as tip 400, 405, or 410 is rotated therein, FIG. 4d illustrates tip 400 wherein the pitch of fins 425 and 435 is 5 mm, tip 405 wherein the pitch of fins 425 and 435 is 10 mm, and tip 415 wherein the pitch of fins 425 and 435 is 15 mm.

Tips 400, 405, and 410 may be manufactured from any suitable materials such that said tips 400, 405, and 410 may be configured to dislodge and remove biofilm from the inner lumen of an endotracheal tube when rotated therein. Such materials may include, plastics, rubbers, silicone, urethane, or other such similar materials. Because it is an object of the present invention to remove biofilm from the inner lumen of an endotracheal tube without damaging said tube, it is desirable that the material from which tips 400, 405, and 410 are manufactured be selected to minimize force and friction applied by tips 400, 405, and 410 to the inner lumen of an endotracheal tube as said tips are rotated therein. Experimentation performed by the inventors herein revealed that tips 400, 405, and 410 exerted less friction on the inner lumen of an endotracheal tube when made from silicone versus urethane. Thus, according to an exemplary embodiment of the present invention, tips 400, 405, and 410 may be made from silicone. In some embodiments, fins 420, 425, 430, and 435 may be made of a softer silicone than cylindrical central portion 415 in order to further limit the risk of damage to an endotracheal tube as tip 400, 405, and/or 410 is rotated therein.

FIGS. 4a-4d illustrate multiple iterations of tips 400, 405, and 410 having various fin configurations and pitches. Each of said iterations is configured to dislodge and remove biofilm from the inner lumen of an endotracheal tube as tip 400, 405, and/or 410 is rotated therein, experimentation was performed to determine the optimal configuration of a tip for the removal of biofilm from an endotracheal tube. To test the various configurations illustrated in FIGS. 4a-4d, lengths of endotracheal tubes were prepared with a set mass of silicone oil along the inner lumen therein, said silicone oil mimicking biofilm that would build up along the inner lumen of an endotracheal tube in an intubated patient. Devices for removing biofilm from the inner lumen of an endotracheal tube comprising a hollow catheter bearing each of the iterations of tips 400, 405, and 410 illustrated in FIGS. 4a-4d were prepared. A testing rig was prepared wherein a motor operating at a set RPM was used to rotate each prepared device as it traversed one of the prepared lengths of endotracheal tubes having silicone oil therein, after which the mass of silicone oil removed by each iteration of tip 400, 405, and 410 was measured to determine the efficacy of each configuration.

Tip 400 having fin 420 with a pitch of 5 mm (FIG. 4a) removed an average of 77.00% of silicone oil across all test runs. Tip 405 having fin 420 with a pitch of 10 mm (FIG. 4a) removed an average of 74.70% of silicone oil across all test runs. Tip 410 having fin 420 with a pitch of 15 mm (FIG. 4a) removed an average of 77.93% of silicone oil across all test runs. Tip 400 having fins 420 and 430, each with a pitch of 5 mm (FIG. 4b) removed an average of 69.82% of silicone oil across all test runs. Tip 405 having fins 420 and 430, each with a pitch of 10 mm (FIG. 4b) removed an average of 72.17% of silicone oil across all test runs. Tip 410 having fins 420 and 430, each with a pitch of 15 mm (FIG. 4b) removed an average of 72.79% of silicone oil across all test runs. Tip 400 having fin 425 with a pitch of 5 mm (FIG. 4c) removed an average of 64.76% of silicone oil across all test runs. Tip 405 having fin 425 with a pitch of 10 mm (FIG. 4c) removed an average of 72.15% of silicone oil across all test runs. Tip 410 having fin 425 with a pitch of 15 mm (FIG. 4c) remove an average of 74.10% of silicone oil across all test runs. Tip 400 having fins 425 and 435, each with a pitch of 5 mm (FIG. 4d) removed an average of 77.52% of silicone oil across all test runs. Tip 405 having fins 425 and 435, each with a pitch of 10 mm (FIG. 4d) removed an average of 76.18% of silicone oil across all test runs. Tip 410 having fins 425 and 435, each with a pitch of 15 mm (FIG. 4d) removed an average of 76.08% of silicone oil across all test runs. Thus, according to an exemplary embodiment of the present invention, the optimal configuration for a tip for a device for removing biofilm from an endotracheal tube may be tip 410 having fin 420 with a pitch of 15 mm, as illustrated in FIG. 4a.

Figure 5:
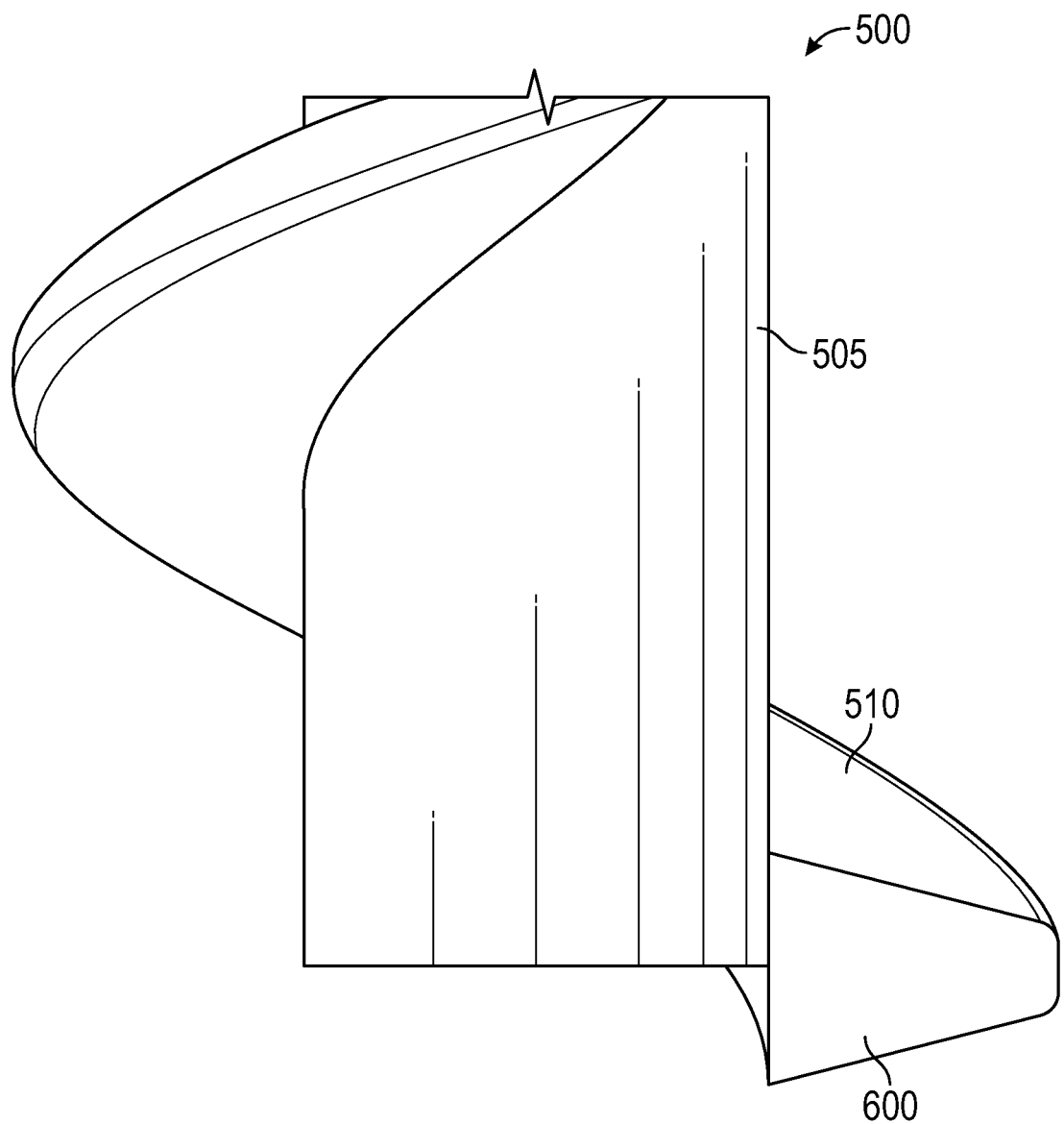
FIG. 5 is a front view of a portion of a tip for a device for removing biofilm from an endotracheal tube, according to an exemplary embodiment of the present invention.

FIG. 5 is a front view of a portion of a tip 500 for a device for removing biofilm from the inner lumen of an endotracheal tube, according to an exemplary embodiment of the present invention. As previously noted, a device for removing biofilm may include a tip 500 having a cylindrical central portion 505 and a fin 510 positioned about the circumference of cylindrical portion 505 to form a helix having a pitch. Fin 510 may have a profile 600. The geometry of profile 600 may be configured to maximize removal biofilm from the inner lumen of an endotracheal tube as fin 510 comes into contact with the inner surface of said tube as the device is rotated. As biofilm is dislodged from the inner lumen of an endotracheal tube as tip 500 rotates therein as it traverses the length of said tube, tip 500 may be further configured to retain said dislodged biofilm against cylindrical central portion 505 within the space defined by the pitch of fin 510.

Figure 6:
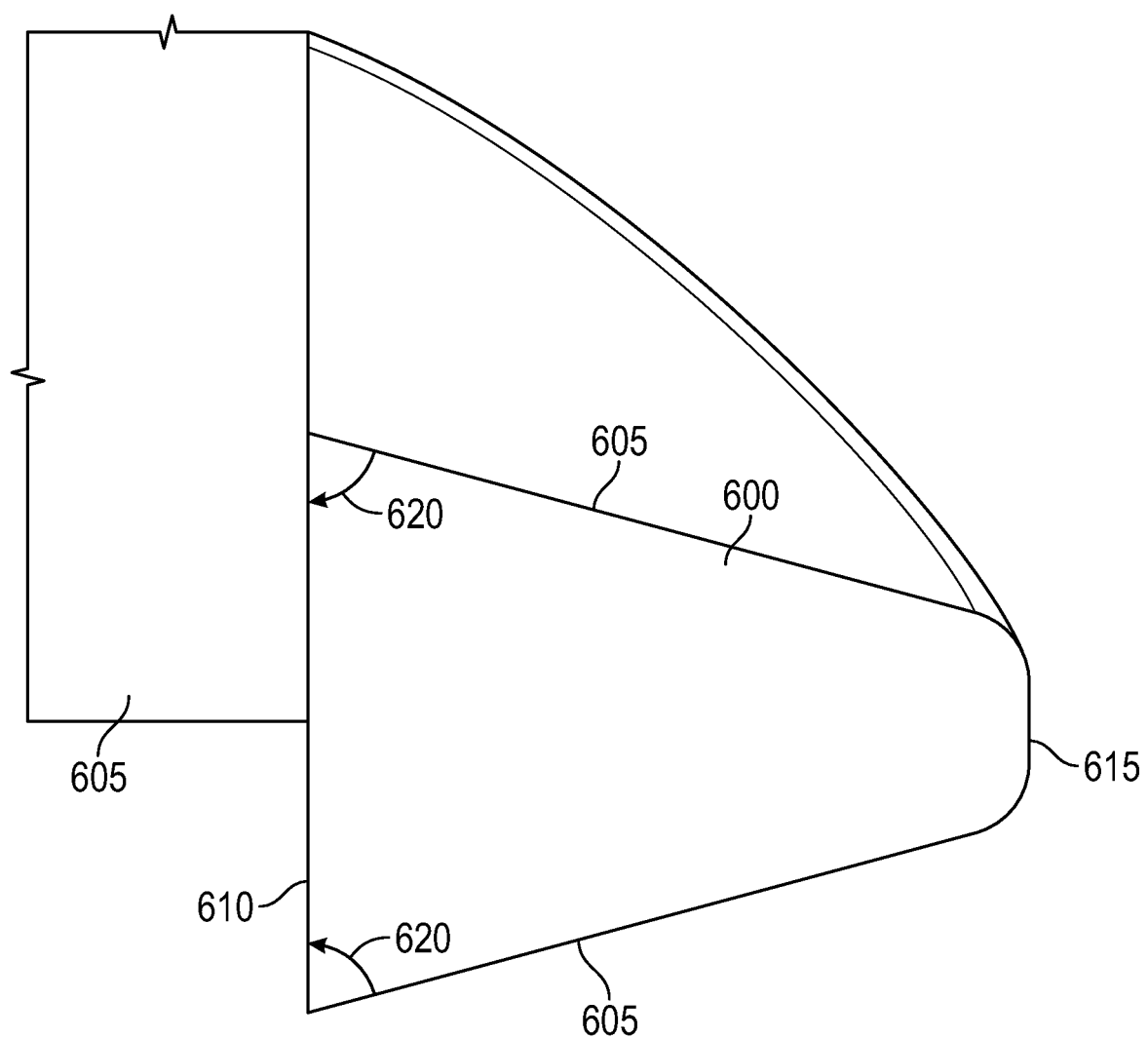
FIG. 6 is a front view of the profile of a fin of a tip for a device for removing biofilm from an endotracheal tube, according to an exemplary embodiment of the present invention.

FIG. 6 is a front view of the profile 600 of a fin 510 of a tip 500 for a device for removing biofilm from an endotracheal tube, according to an exemplary embodiment of the present invention. While the profile 600 of such a fin may be any shape configured to dislodge and remove biofilm from the inner lumen of an endotracheal tube as discussed herein, according to an exemplary embodiment of the present invention, profile 600 may be approximately the shape of a trapezoid having legs 605, larger base 610, smaller base 615, and base angles 620. Profile 600 may be configured such that larger base 610 connects to cylindrical portion 605, and smaller base 615 makes contact with the inner lumen of an endotracheal tube and is configured to dislodge biofilm therefrom as tip 500 rotates therein. Smaller base 610 may be configured to have rounded edges where it connects to legs 605 to eliminate sharp edges that may damage an endotracheal tube as tip 500 rotates therein. According to an exemplary embodiment of the present invention, base angles 605 may be equal, such that profile 600 is an approximate isosceles trapezoid. In some such embodiments, base angles 605 may be seventy-five degrees.

Figure 7:
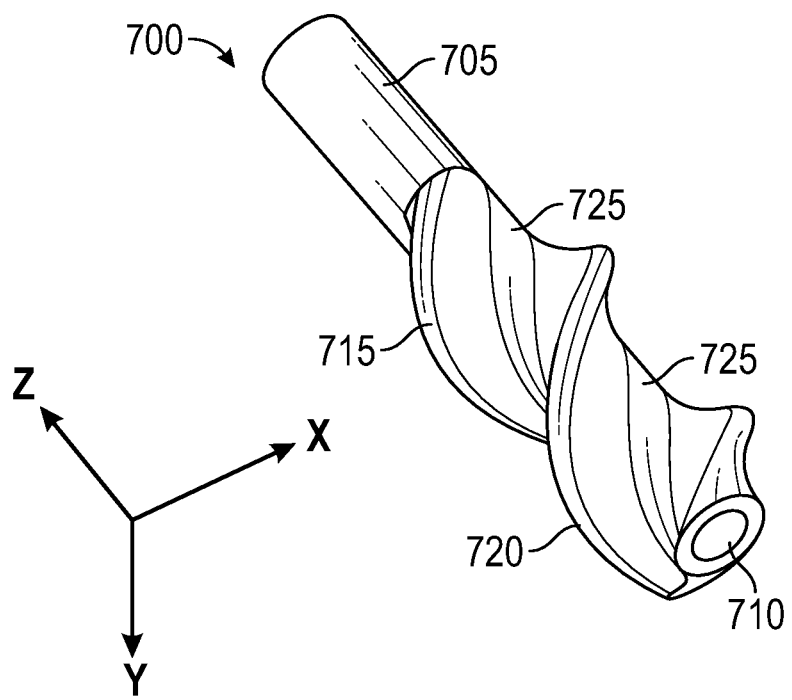
FIG. 7 is an isometric view of a tip for a device for removing biofilm from an endotracheal tube, according to an exemplary embodiment of the present invention.

As discussed with respect to FIG. 4, the tip of a device for the removal of biofilm from the inner lumen of an endotracheal tube need not be limited to a single fin. For example, FIG. 7 is an isometric view of a tip 700 for a device for removing biofilm from an endotracheal tube, according to an exemplary embodiment of the present invention. Tip 700 may include cylindrical central portion 705, which may have a hollow longitudinal channel 710 to allow for the passage of air through tip 700. Tip 700 may further comprise fins 715 and 720 each of which may be configured to spiral about the circumference of cylindrical central portion 705 in the shape of a helix. The helical shapes of fins 715 and 720 may define channel 725 positioned against cylindrical central portion 705 between fins 715 and 720. Thus, tip 700 may be configured such that as it rotates within an endotracheal tube having biofilm on its inner lumen, fins 715 and 720 shear or otherwise dislodge said biofilm from the endotracheal tube such that the dislodged biofilm is retained within channel 725 until tip 700 is removed from the tube, or until the dislodged biofilm is removed by other means, such as a vacuum or other similar device configured to create a suction force. In some embodiments of the present invention, beginning at the distal edge of cylindrical portion 705 and moving in a proximal direction, each of fin 715 and 720 spirals around cylindrical portion 705 in the shape of a helix at a distance of 20 mm per revolution. Each of fin 715 and 720 may further include a taper cut of 30 degrees at the proximal and distal ends.

Figure 8:
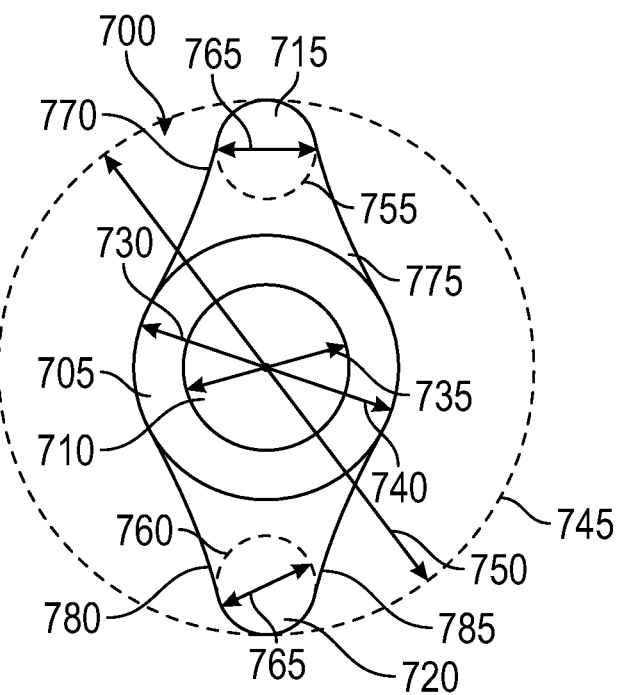
FIG. 8 is a top cross section view of a tip for a device for removing biofilm from an endotracheal tube, according to an exemplary embodiment of the present invention.

FIG. 8 is a top cross section view of tip 700 for a device for removing biofilm from an endotracheal tube, according to an exemplary embodiment of the present invention. The size of tip 700 may be selected or scaled in accordance with the diameter of the endotracheal tube to be cleaned. For example, in an embodiment of the present invention for cleaning the inner lumen of an 8 mm endotracheal tube, cylindrical central portion 705 may have outer diameter 740 of 4.0 mm. Inner diameter 745, which corresponds with the diameter of longitudinal channel 710, may be 2.5 mm. Tip 700 may thus be configured such that circle 745 has diameter 750 of 8.0 mm and is concentrically aligned with the circles having diameter 730 and 735. The cross section of 700 may be further configured such that the surfaces of fins 715 and 720 are arcs of circles 755 and 760, respectively, each of which have diameter 765 of 1.5 mm. Moreover, the remainder of the cross section of the surface of fin 715 may be defined by arcs 770 and 775, each of which is an arc of a circle having a diameter of 11.5 mm. Arc 770 is tangent to circle 755 and the circle having diameter 740 which defines cylindrical central portion 705. Arc 775 is also tangent to circle 755 and cylindrical central portion 705, but 180 degrees around said circle 755 and cylindrical central portion 705 such that arc 775 defines the opposite side of the cross section of fin 715 from arc 770. Similarly, the remainder of the cross section of the surface of fin 720 may be defined by arcs 780 and 785, each of which is an arc of a circle having a diameter of 11.5 mm. Arc 780 is tangent to circle 755 and the circle having diameter 740 which defines cylindrical central portion 705. Arc 785 is also tangent to circle 755 and cylindrical central portion 705, but 180 degrees around said circle 755 and cylindrical central portion 705 such that arc 785 defines the opposite side of the cross section of fin 715 from arc 770. As noted, the exemplary embodiment of the present invention illustrated in FIGS. 7 and 8 is optimized for an endotracheal tube having an inner diameter of 8 mm. However, the illustrated embodiment can be scaled for endotracheal tubes of other diameters by, for example, uniformly scaling tip 700 along the X and Y axes as illustrated in FIG. 7.

Figure 9:
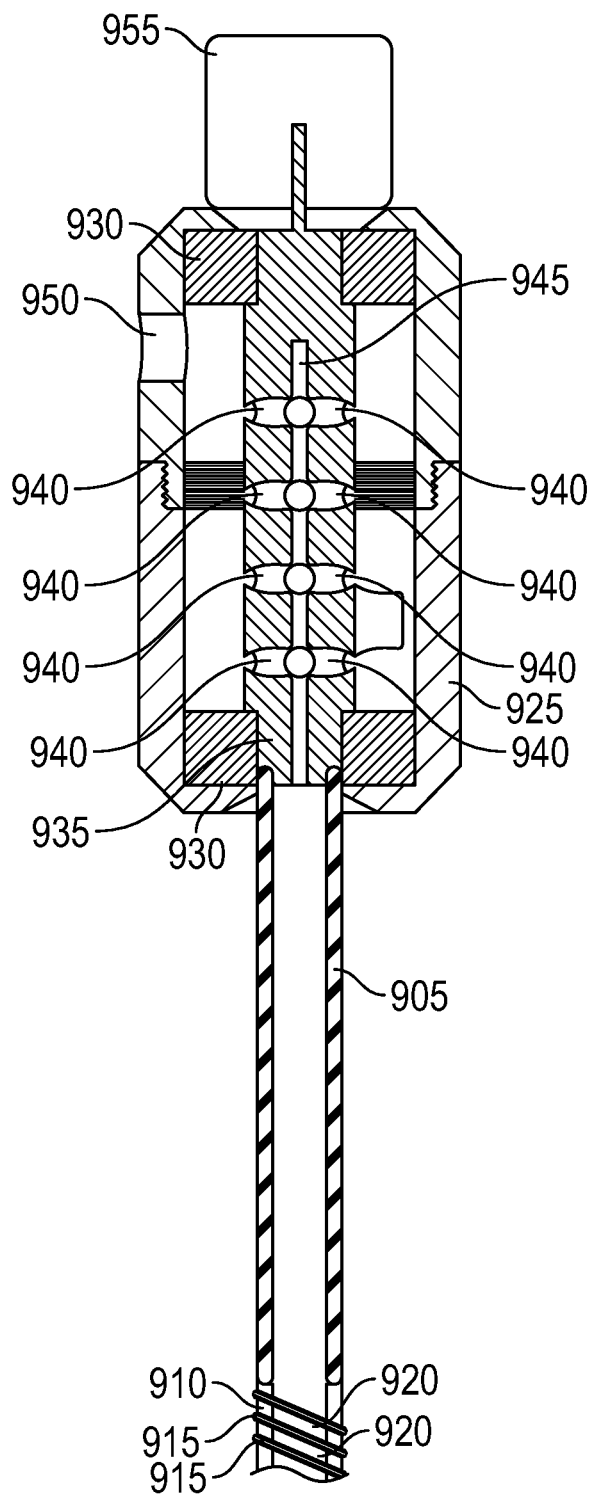
FIG. 9 is a top cross section view of a device for removing biofilm from an endotracheal tube, accordingly to an exemplary embodiment of the present invention.

FIG. 9 is a top cross section view of a device for removing biofilm from an endotracheal tube, accordingly to an exemplary embodiment of the present invention. As with other embodiments, device 900 may include hollow catheter 905 and tip 910 attached to the distal end of catheter 905. Tip 910 may comprise a hollow cylindrical central portion and a fin 915 and configured such that fin 915 wraps around said hollow cylindrical portion in the shape of a helix having a pitch such that fin 915 defines a channel 920 adjacent to the cylindrical central portion between the pitch of fin 915. Tip 910 may further comprise a hollow longitudinal channel through the cylindrical central portion that, when attached to catheter 905, aligns with the hollow center of catheter 905 to allow the passage of air through catheter 905 and tip 910.

Device 900 may further comprise housing 925, which may include shaft 935, one or more bearing and seal combinations 930, and opening 950. Because it is an object of the present invention that device 900 be used to clean an endotracheal tube of an intubated patient without extubating said patient, device 900 may be configured such that ventilated air passing through device 900 remain in a sealed environment separate from the ambient air in the environment outside device 900. To that end, in some embodiments of the present invention, opening 950 may be configured to receive a ventilator hose, wherein said may be connected to a ventilator providing mechanical ventilation to a patient. Thus, device 900 may be configured to allow the passage of air and other gases to and from said ventilator through device 900 as it is used to clean the inner lumen of an endotracheal tube of an intubated patient.

Specifically, while device 900 is inserted into an endotracheal tube of an intubated patient, air and other gases, such as oxygen, may be delivered to said endotracheal tube from said ventilator through said ventilator hose. Said air and other gasses may pass into the interior of housing 925 through opening 950, then travel through plurality of holes 940 into the hollow longitudinal channel 945 of shaft 935, into hollow catheter 905, and then into said endotracheal tube through tip 910. Other gases, such as carbon dioxide, may travel back to said ventilator via the reverse of the aforementioned path, i.e., through tip 910 into hollow catheter 905, into the longitudinal channel 945 of shaft 935, through holes 940 into the interior of housing 925, then back to the ventilator through opening 945. To keep ventilator supplied air sealed off from the environment surrounding device 900, bearing and seal combination 930 at the distal end of housing 925 may be configured such that catheter 905 passes through the wall of housing 925 such that it connects to shaft 935. Bearing and seal combination 930 at the distal end of housing 925 may be further configured to allow shaft 935 and catheter 905 to rotate longitudinally while simultaneously preventing air and other gases within housing 925 from escaping housing 925—or from entering housing 925 from the external environment—where catheter 905 enters housing 925. Similarly, bearing and seal combination 930 positioned at the proximal end of housing 925 may be configured to allow a portion of shaft 935 to protrude from the proximal end of housing 925 such that a torque may be applied to said protruding portion of shaft 935 thereby resulting in a rotational motion to the combination of shaft 935, catheter 905, and tip 910. Thus, said bearing and seal combination 930 at the distal end of housing 925 may be further configured to allow shaft 935 to rotate longitudinally while simultaneously preventing air and other gases within housing 925 from escaping housing 925—or from entering housing 925 from the external environment—where said portion of shaft 935 protrudes from the proximal end of housing 925.

In certain embodiments of the present invention, the combination of shaft 935, catheter 905, and tip 910 may be rotated by applying a torque to the portion of shaft 935 protruding from the proximal end of housing 925. Said torque may be applied manually, or via motor 955. Thus, in certain embodiments, motor 955, which may be an electric motor, may be configured to deliver a torque to the combination of shaft 935, catheter 905, and tip 910.

While the embodiments of the present invention are described herein with reference to various implementations and exploitations, it will be understood that these embodiments are illustrative and that the scope of the invention(s) is not limited to them. In general, embodiments of a device for separating tissue during dissection as described herein may be implemented using methods, facilities, devices, and materials consistent with any appropriate structure as described or illustrated herein. Many variations, modifications, additions, and improvements are possible.

For example, plural instances may be provided for components, operations, or structures described herein as a single instance. Boundaries between various components, operations, and functionality are depicted somewhat arbitrarily, and particular operations are illustrated within the context of specific illustrative configurations. In general, structures and actions presented as separate components or steps in the exemplary configurations may be implemented as a combined structure or step. Similarly, structures and actions presented as a single component or step may be implemented as separate components or steps. These and other variations, modifications, additions, and improvements may fall within the scope of the inventive subject matter.

What is claimed is:

1. A device for removing biofilm from an inner surface of an endotracheal tube, comprising:
   a hollow catheter having a proximal end, a distal end, and a longitudinal axis,
   a tip having a longitudinal axis, said tip comprising:
      a cylindrical central portion having a hollow longitudinal channel, and
      a fin having a helical shape and a pitch; and
   a housing having a proximal end and distal end at said proximal end of said hollow catheter, said housing comprising:
      a cylindrical shaft having a proximal end, a distal end, a central longitudinal channel and a plurality of holes on a surface of said shaft, each of the plurality of said holes leading to said longitudinal channel, and
      an opening;
   wherein said tip is connected to said distal end of said hollow catheter such that said longitudinal axis of said tip aligns with said longitudinal axis of said hollow catheter;
   wherein said fin is positioned about a circumference of said cylindrical central portion of said tip such that the pitch of said fin defines a channel along the circumference of said cylindrical central portion;
   wherein said hollow catheter and said tip are configured to rotate about said longitudinal axes such that said fin has a rotational motion;
   wherein the combination of said tip and said hollow catheter is configured to be inserted, tip-first, into an endotracheal tube having biofilm on the inner surface of said endotracheal tube;
   wherein said fin is configured to contact the inner surface of said endotracheal tube such that said rotational motion of said fin dislodges said biofilm from the inner surface of said endotracheal tube;
   wherein said fin is further configured to retain said dislodged biofilm within said channel along the circumference of said cylindrical central portion;
   wherein said hollow catheter and said hollow longitudinal channel are configured such that airflow through said endotracheal tube is not interrupted while said device is inserted therein;
   wherein the distal end of said housing is configured to receive said proximal end of said hollow catheter;
   wherein the proximal end of said hollow catheter connects to the distal end of said cylindrical shaft such that a rotational force applied to said cylindrical shaft is also applied to said hollow catheter;
   wherein the proximal end of said housing is configured to allow a portion of said cylindrical shaft to protrude from the proximal end of said housing;
   wherein said portion of said cylindrical shaft protruding from the proximal end of said housing is configured such that a torque applied to said portion results in the rotation of said cylindrical shaft, said hollow catheter, and said tip; and
   wherein said opening, said plurality of holes, said longitudinal channel of said cylindrical shaft, said hollow catheter, and said hollow longitudinal channel of said tip are configured such that airflow through said endotracheal tube is not interrupted while said tip and said hollow catheter are inserted therein.

2. The device of claim 1, wherein said opening is further configured to receive a ventilator hose connected to a ventilator;
   wherein said housing is further configured to prevent air delivered by said ventilator into said housing from escaping into the exterior environment; and
   wherein said housing is further configured to prevent air in the exterior environment from entering said housing.

3. The device of claim 2, wherein said fin is further configured to be an approximate trapezoidal prism such that a cross section of said fin taken along a plane that includes said longitudinal axis of said tip, is an approximate trapezoid having a larger base, a smaller base, an upper side, a lower side, equivalent base angles defined by the larger base and each of said upper side and said lower side, an upper edge defined by the connection between said smaller base and said upper side, and a lower edge defined by the connection between said smaller base and said lower side;

wherein said larger base is adjacent to said cylindrical central portion; and wherein said smaller base is configured to contact the inner surface of said endotracheal tube such that said rotational motion of said fin dislodges said biofilm from the inner surface of said endotracheal tube.

4. The device of claim 3, wherein said fin is further configured such that said equivalent base angles are seventy-five degrees.

5. The device of claim 4, wherein said fin is further configured such that said smaller base is an arc such that said upper edge and said lower edge are rounded.

6. The device of claim 5, wherein said pitch is one of 5 mm, 10 mm, and 15 mm.

7. The device of claim 6, wherein said tip is manufactured from one of silicon and urethane.

8. The device of claim 7, further comprising:

a motor;

wherein said motor is positioned at the proximal end of said housing;

wherein said motor is configured to deliver a torque to said portion of said cylindrical shaft protruding from the proximal end of said housing such that said torque rotates the combination of said cylindrical shaft, said hollow catheter, and said tip.

* * * * *